United States Patent [19]

Miller et al.

[11] Patent Number: 4,666,672
[45] Date of Patent: May 19, 1987

[54] OPTRODE FOR SENSING HYDROCARBONS

[75] Inventors: Holly Miller, Bethel Island; Fred P. Milanovich, Lafayette; Tomas B. Hirschfeld, Livermore; Fred S. Miller, Bethel Island, all of Calif.

[73] Assignee: University of California, Berkeley, Calif.

[21] Appl. No.: 721,150

[22] Filed: Apr. 8, 1985

[51] Int. Cl.⁴ .............................................. G01N 21/64
[52] U.S. Cl. ...................................... 422/68; 128/632; 436/126; 436/172; 436/178
[58] Field of Search ................ 250/461.1; 356/37, 318, 356/445; 422/68, 58; 436/163, 172, 178; 128/632, 634, 635, 633

[56] References Cited

U.S. PATENT DOCUMENTS

| | | |
|---|---|---|
| 3,472,626 | 10/1969 | Law . |
| 4,200,110 | 4/1980 | Peterson et al. .................... 128/634 |
| 4,272,485 | 6/1981 | Lubbers ................................ 422/68 |
| 4,321,057 | 3/1982 | Buckles ................................ 422/68 |
| 4,476,870 | 10/1984 | Peterson et al. .................... 128/634 |
| 4,548,907 | 10/1985 | Seitz et al. .......................... 436/172 |
| 4,577,109 | 3/1986 | Hirshfield ......................... 250/461.1 |

OTHER PUBLICATIONS

Fujiwara, Abhandl. Natur. Ges. Rostock., 6, 33 (1916).
Daroga et al., J. Chem. Soc. Ind, 60, 218 (1940).
Hunold et al, Anal. Chem., 179, 81 (1961).
Lugg, Anal. Chem., 38, 1532 (1966).
Uno et al, Chem. Pharm. Bull., 30, 1876 (1982).
Hirschfeld et al, NLR No. UCID-19774, Livermore Ca. (1983).
Hirschfeld et al, Opt. Eng., 22(5), 527(1983).
Milanovich, NLR UCRL-89181, May 1983.
Milanovich et al, TRC AD-89-F-2A074, EPA-1984.
Miller et al, NLA-UCRL 91350 Mar. 1983.

*Primary Examiner*—Michael S. Marcus
*Attorney, Agent, or Firm*—Shyamala T. Rajender; Berthold J. Weis

[57] ABSTRACT

A two-phase system employing the Fujiwara reaction is provided for the fluorometric detection of halogenated hydrocarbons. A fiber optic is utilized to illuminate a column of pyridine trapped in a capillary tube coaxially attached at one end to the illuminating end of the fiber optic. A strongly alkaline condition necessary for the reaction is maintained by providing a reservoir of alkali in contact with the column of pyridine, the surface of contact being adjacent to the illuminating end of the fiber optic. A semipermeable membrane caps the other end of the capillary tube, the membrane being preferentially permeable to the halogenated hydrocarbon and but preferentially impermeable to water and pyridine. As the halogenated hydrocarbon diffuses through the membrane and into the column of pyridine, fluorescent reaction products are formed. Light propagated by the fiber optic from a light source, excites the fluorescent products. Light from the fluorescence emission is also collected by the same fiber optic and transmitted to a detector. The intensity of the fluorescence gives a measure of the concentration of the halogenated hydrocarbons.

6 Claims, 6 Drawing Figures

OPTRODE FOR SENSING HYDROCARBONS

The United States Government has rights in this invention pursuant to Contract No. W-7405-ENG-48 between the University of California and the United States Department of Energy.

BACKGROUND OF THE INVENTION

The subject invention relates generally to optical fiber spectrometry and more specifically to the fluorometric detection of polyhalogenated hydrocarbons.

The detection and measurement of bound halogens and halogen related compounds in human and animal tissues and in industrial effluents is of vital importance for health and environmental purposes. Many common household and industrial chemicals in every day use, such as dry cleaning agents, refrigerants like freon, fire extinguishers, paint removers, fumigants, polymeric compounds, anesthetics such as halothane, enfluorane, metoxofluorane and isofluorane, and some antihelmintics, certain pesticides and fungicides contain toxic, halogenated organic compounds which are either ingested or discharged into the environment, making these chemicals a potential, and in most instances, a real health and environmental hazard. It has thus become important to be able to detect and even quantitatively measure or monitor the presence of these compounds or their metabolic products, so that the levels of their ingestion or discharge into the environment may be controlled.

As a consequence, several methods and instruments have been devised to measure these halogen containing organic compounds. Some of these methods for detecting gaseous halohydrocarbons use electron capture or piezo electric devices. Some other methods have been devised to detect organic halocompounds, especially in the liquid or aqueous phase. One such method is based on the reaction of halogenated hydrocarbons with pyridine or pyridine derivatives in an alkaline medium to yield highly colored products. It is known in the art that when a gem-polyhalogen compound, which is a compound that carries more than two halogen atom on the same carbon, is heated with pyridine in a strongly alkaline medium (pH 10-11), such as in the presence of sodium or potassium hydroxide, an intensely red product, exhibiting absorption maxima at about 368 mu and at about 535 mu, is formed. This reaction scheme, shown in equation 1 below,

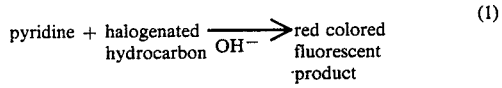

(1)

is known as the Fujiwara reaction (K. Fujiwara, Sitzfer, Abhandl. Naturforsch. Ges. Rostock., 6, 33, (1941); G. A. Lugg, Anal. Chem., 38, 1532 (1966); T. Uno et al., Chem. Pharm. Bull., 30, 1876 (1982)). The Fujiwara reaction has become a classic method for the detection of halogenated hydrocarbons in a given sample or analyte in the liquid phase. However, for a quantitative measure of halogenated hydrocarbons in an analytical or test solution or sample, the Fujiwara reaction presents some problems, due to the insolubility of pyridine in reagents normally used to generate the necessary alkalinity and the difficulty in being able to control the rate of diffusion of the OH$^-$ ion from the aqueous phase into the organic pyridine phase.

More often, the reaction consists of a two-phase procedure whereby the gem-polyhalogen compound, pyridine and aqueous sodium or potassium hydroxide are combined, mixed, and heated for a predetermined length of time until an intensely red color develops. The pyridine phase is then separated from the alkaline phase by conventional methods. Absorption spectra of the colored product are measured thereafter. The amount of the chromophoric product formed is dependent on the amount and rate of diffusion of the hydroxide ion into the pyridine phase of the mixture. Since this diffusion is difficult to control, reproducibility of measurements becomes extremely difficult and unpredictable.

A one phase procedure using pyridine-water-sodium hydroxide has also been employed to avoid the pitfalls of the two phase method (G. A. Lugg, supra). There have also been several modifications of the Fujiwara reaction, such as different solvents, different bases, varying temperatures, varying concentrations of sodium hydroxide, time of reaction and the like, to minimize the difficulties encountered and to make the reaction more widely accessible.

U.S. Pat. No. 3,472,626 issued to Law, discloses a method for the detection of organic halogen containing compounds in aqueous liquids, by the use of the salt of a pyridine base and either caustic soda or caustic potash.

Still other problems are encountered in the measurement of these halogenated hydrocarbons or their metabolic products in environmental and tissue samples. These compounds are found at extremely low levels in tissues, groundwater samples or effluents, which tend to make the reproducibility and reliability of any measurements difficult. It would also be desirable some times to be able to analyze these samples at a discharge site which is remote from the site of the detection equipment and continually monitor the levels of these compounds in various samples from a remote monitoring site.

Laser based remote fiber spectroscopy offers a wide range of possibilities for the in situ detection and quantification of not only halohydrocarbons but also other groundwater contaminants. The development of high transmission, long range fiber optics and the advantages of their use in data transmission have made fiber optical methods of data transmission and detection extremely attractive. The use of such fiber optics also makes it possible to trasmit or receive data signals over distances of two or three kilometers.

It would, therefore, be desirable to have a fiber optic sensor and detection system, for the measurement of organic halohydrocarbons in tissue and environmental samples, which would not only be sensitive to measure low levels of these compounds but which would also be amenable to operation from a remote location.

Accordingly, it is an object of the subject invention to provide a method for the measurement of organic halohydrocarbons in environmental and tissue samples.

Another object is to provide a method whereby the levels of organic halohydrocarbons in tissue, ground water and other environmental samples can be continually monitored.

Yet another object is to provide an apparatus and method which enable the simultaneous monitoring of organic halohydrocarbons in multiple samples of groundwater and other environmental material and tissue samples, from a remote location.

Still another object is to provide a sensor and detection system which can detect not only low levels of organic halohydrocarbons but can also be operated from a remote location.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the subject invention is directed to an "optrode" and a method for the detection of halohydrocarbons, particularly organic chlorides, in an analyte which may be tissue, groundwater, or other environmental samples. As used herein, an optrode is a chemical sensor device located at the interface between an optical fiber and the halohydrocarbon of interest (the analyte) contained in a sample solution. The basic design of the optrode, according to one aspect of the subject invention, includes an optical fiber terminus comprising a porous substrate such as polyvinyl alcohol (PVA) or control pore glass (CPG). Appropriate hygroscopic additives may be included in the PVA or CPG to maintain the necessary water content. The PVA or CPG can be charged with specific chemical reagents which when exposed to target molecules, form a chemically or physically detectable product such as for example, either a fluorescent or fluorescence-quenching product.

In one embodiment of the instant optrode, a two-phase reagent system is placed in a capillary tube and an optical fiber is placed inside the capillary tube such that one end of it is either adjacent to the interface of the two-phase reagent system or extends into the two-phase reagent system and the other end is connected to an appropriate illumination source and a detector system. For the detection of halohydrocarbons, an exemplary two-phase reagent system may comprise pyridine or a pyridine derivative and an alkaline reagent such as potassium or sodium hydroxide, the two reagents being layered over each other such that there is a surface of contact between the two. The fiber optic illuminates the column of the pyridine or pyridine derivative trapped in the capillary tube, which is coaxially attached at one end to the illuminating end of the fiber optic. A strongly alkaline condition necessary for the reaction is maintained by the reservoir of alkali in contact with the column of pyridine, the surface of contact being adjacent to the illuminating end of the fiber optic. Optionally, a semipermeable membrane caps the other end of the capillary tube, the membrane being preferentially permeable to the halogenated hydrocarbon and but preferentially impermeable to water and pyridine. Alternatively, an air bubble may be interposed between the test solution and the pyridine phase. As the halogenated hydrocarbon diffuses through the membrane and into the column of pyridine, fluorescent products are formed from the reaction of the halohydrocarbon with the pyridine in the presence of the $OH^-$ ions. The optical fiber transmits light from the illuminating source such as a suitable laser source, to the interface of the two-phase reagent system where the analyte in the test solution reacts with the pyridine. It also transmits the fluorescent light back to the detection system. Suitable laser sources include argon laser, carbon dioxide laser, ruby laser, copper vapor laser and the like.

One embodiment of the subject method utilizes laser based remote fiber spectrometry for the detection and measurement of trace to macro concentrations of halogenated hydrocarbons from single or multiple samples, from the same location or multiple locations, at a site remote from the detection system. A laser light of the appropriate wavelength is focused into single strand optical fibers or cables. The optical fibers are coupled to the samples of the analyte at various locations or from the same locus through the optrodes. The light, after interaction with the analyte, is collected and transmitted back through the same optical fibers or cables to a specially designed detection system such as a spectrometer where the returning light is spectrally sorted and analyzed.

Another aspect of the subject invention is a method for the detection of low levels of polyhalogenated hydrocarbons comprising a modified Fujiwara reaction (equation 1). The method, broadly, comprises containing pyridine or pyridine derivatives in a suitable container and layered over an alkaline medium such as potassium or sodium hydroxide, such that there is a surface of contact between the pyridine and alkali layers. When exposed to a solution of the halohydrocarbon, or to a solution suspected of containing the analyte, the pyridine reacts with the halohydrocarbon in the presence of the alkali to yield a bright red to a reddish brown, fluorescent product. This fluorescent product is illuminated at an appropriate wavelength and the fluorescence emission of the product is measured as a function of time or the concentration of the halohydrocarbon. The optrode is positioned adjacent the surface of contact, and in conjunction with a detection system such as a fluorimeter or spectrometer. The amount and rate of formation of the product formed may be measured continually or at predetermined time intervals. The detection system may also be located at a site remote from the site of measurement.

A preferred embodiment of the optrode or the sensor system of the subject invention comprises a capillary tube or cuvette, 0.1 mm to 2 mm in internal diameter, preferably capped at one end. Capping, however, is not critical for the operation of the optrode. The capping material is either porous or semipermeable, preferably semipermeable. The most preferred capping material is a water impermeable membrane which is also impermeable to pyridine, but permeable to halohydrocarbons. Exemplary membrane materials include but are not limited to parafilm (thin paraffin films), mylar, electrostatically treated mylar, zeflour, polycarbonate films and the like and exemplary halohydrocarbons detectable by the method include but are not limited to gem-halohydrocarbons such as chloroform, methylchloroform, sym-tetrachloroform, phenylchloroform, carbon tetrachloride, dichloromethane, trichloroethylene, 1,1,2-trichloroethane and the like.

The instant method and optrode are suitable for monitoring volatile organic chloride contaminants in aqueous systems. The subject optrode is able to detect and quantify sub-part-per-million to macro concentrations of organic chlorides in aqueous solutions. The fiber optic system used in the subject invention enables the measurement of organic chloride where the sample and detection system are separated by a distance of greater than 500 meters of optical fiber. It is also possible by the use of the subject method to simultaneously measure organic chloride content in multiple samples from the same location or from different locations that are separated by several hundred meters. The subject method is specific to organic compounds containing two or more chlorines and sensitive to approximately 0.1 part per million, and reproducible within about ±3%.

BRIEF DESCRIPTION OF THE DRAWINGS

The accompanying drawings, which are incorporated into and form a part of the specification, illustrate one embodiment of the invention and, together with the description, serve to explain the principles of the invention. In the drawing:

FIG. 5 shows absorption spectra at 530 nm of pyridine containing varying amounts of $CHCl_3$.

DETAILED DESCRIPTION OF THE INVENTION

Figure 1:
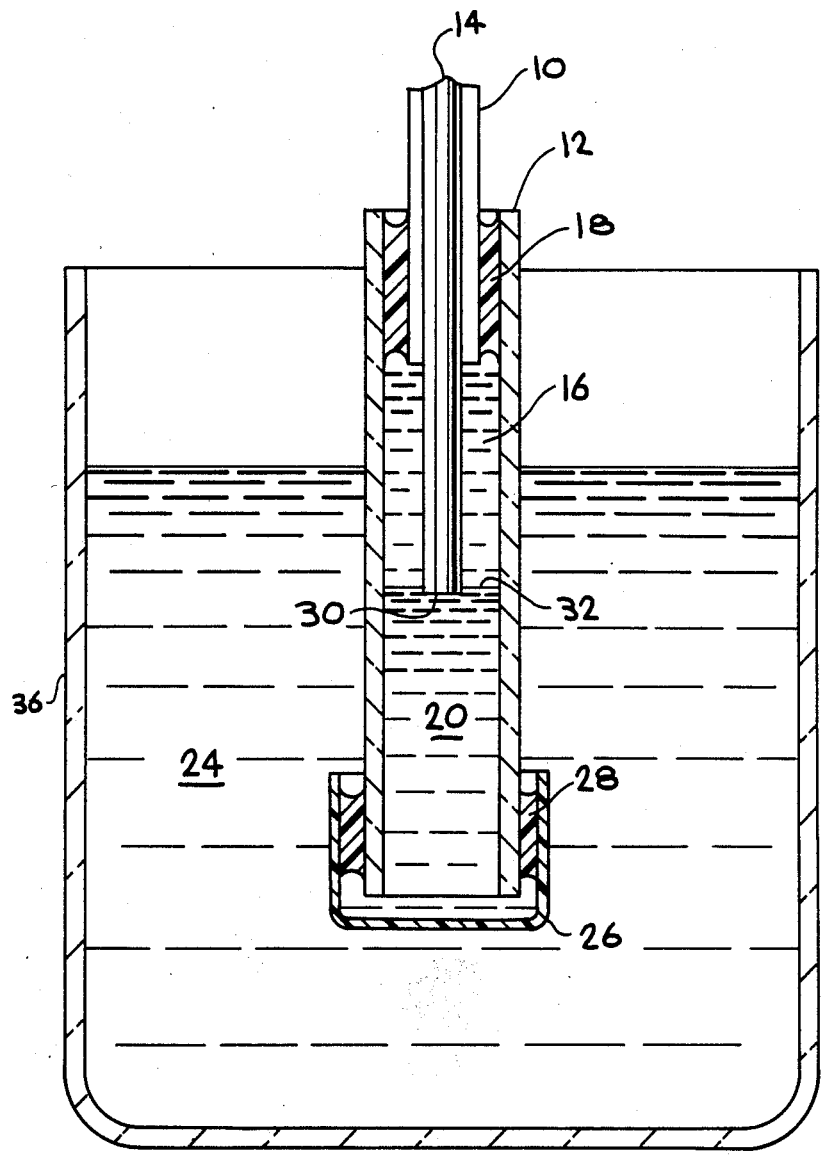
FIG. 1 gives a cross-sectional view of the optrode shown immersed in a test solution.

The subject invention is broadly directed to an apparatus and method for the detection and measuring continually or at predetermined intervals, of organic halohydrocarbons. The key component of the apparatus is termed the "optrode" which is a special termination at the distal end of an optical fiber, which aids in the increase, decrease or initiation of a measurable reaction or signal when an illuminating beam of light interacts with the species to be measured. The illuminating light may be in the UV, visible or infrared regions. Suitable illuminating sources may be any conventional sources and include but are not limited to lasers, such as argon, $CO_2$, ruby, copper vapor and the like. Argon laser is most conveniently used. As used herein, an optrode is, more specifically, a chemical sensor device used at the interface between an optical fiber and a sample solution containing the halohydrocarbon of interest (the analyte). The basic design of the optrode, according to one aspect of the subject invention, is the terminus of a plain optical fiber. According to another aspect of the instant invention, the optrode includes an optical fiber terminus optionally comprising a porous substrate such as polyvinyl alcohol (PVA) or control pore glass (CPG). When PVA or CPG termini are used, appropriate hygroscopic additives may be included in the PVA or CPG to maintain the necessary water content. The PVA or CPG can be charged with specific chemical reagents which when exposed to target molecules, form a chemically or physically detectable product such as for example, either a fluorescent or fluorescence-quenching product.

The general principles of the operation of optrodes and the design and construction of some optrodes are described in pending patent application U.S. Ser. No. 06/445,619 filed Nov. 30, 1982 which is a continuation-in-part of U.S. Ser. No. 194,684 filed Oct. 6, 1980, both of which are incorporated herein by reference and made a part hereof.

Although many types of optrodes have been described, monitoring optrodes, such as the optrode of the instant invention, however, have to meet stringent requirements and applications. These optrodes, can be either physical or chemical in nature. Physical optrodes are mechanical and direct measuring whereas chemical optrodes, generally, utilize reagents and membranes. These reagents may be immobilized on suitable matrices or substrates or contained in appropriate reservoirs. Chemical optrodes can be used to measure both physical and chemical properties. Measurement of fluorescence, absorption and reflection are all suitable parameters for optrode applications. Fluorescence is most often chosen because of its high sensitivity, reasonable specificity and the variety of indicators that are available. In some instances, a fluorescent tag may be attached to a suitable reagent, thereby expanding the availability of appropriate sensing systems.

However, several factors need to be taken into consideration in the design and construction of a chemical optrode. Such factors include but are not limited to (1) the selection of an appropriate chemical reaction which can be monitoring by means of some measurable parameter, (2) the feasibility of fixing the necessary reagents on the fiber, (3) possible interference or poisoning of the optrode by extraneous components of the sample matrix, and (4) the active and shelf life of the particular optrode.

There are three basic types of chemical optrodes. In two of these, the reagent is immobilized. In one, the reagent is trapped in a polymer matrix and in the second, it is attached to glass beads or glass rods by covalent bonds and then glued or welded to optical fibers. The third type of optrode is the reservoir type where the reagent is contained in a reservoir which is separated by a suitable membrane from the sample or analyte. The reaction takes place on the surface of the membrane and the measurable signal, such as fluorescence, is emitted from the surface of the membrane. This type of optrode is particualrly suitable when a non-reversible chemical reaction is involved and a continuous source or replenishment of the reagent is required.

The "optrode" of the subject invention is of the third type and is a chemical sensor device used at the interface between an optical fioer and a sample solution of an analyte. The basic design of the optrode of the subject invention, according to one aspect of the subject invention, is the terminus of a plain optical fiber. According to another aspect of the instant invention, the optrode includes an optical fiber terminus optionally comprising a porous substrate such as polyvinyl alcohol (PVA) or control pore glass (CPG). When PVA or CPG termini are used, appropriate hygroscopic additives may be included in the PVA or CPG to maintain the necessary water content. The PVA or CPG can be charged with specific chemical reagents which when exposed to target molecules, form either a fluorescent or fluorescence-quenching product. Appropriate hygroscopic additives maintain the necessary water content in the PVA or CPG.

In the subject optrode, a two-phase reagent system is placed in a capillary tube and the optical fiber is placed inside the capillary tube such that one end of it is adjacent the interface of the two-phase reagent system and the other end is connected to an appropriate illumination source and a detector system. For the detection of halohydrocarbons, an exemplary two-phase reagent system employed may comprise a pyridine derivative and an alkaline reagent such as potassium or sodium hydroxide, the two reagents being layered over each other such tnat there is a surface of contact between the two. As used herein, the term pyridine derivative includes without limitation, pyridine, salts thereof, substituted pyridine, and related compounds. The fiber optic illuminates the column of the pyridine or pyridine derivative trapped in the capillary tube which is coaxially attached at one end to the illuminating end of the fiber optic. A strongly alkaline condition necessary for the reaction is maintained by the reservoir of alkali in contact with the column of pyridine, the surface of contact being adjacent to the illuminating end of the fiber optic. Optionally, a semipermeable membrane caps the other end of the capillary tube, the membrane being preferentially permeable to the halogenated hydrocarbon and but preferentially impermeable to water and pyridine. Alternatively, an air bubble may be interposed between the test solution and the pyridine phase. As the halogenated hydrocarbon diffuses through the membrane and into the column of pyridine, fluorescent reaction products are formed. One end of the optrode is connected to the detector and the other end interacts with the test solution. The optical fiber transmits light from the illuminating source such as a suitable laser source, to the interface of the two phase reagent system where the analyte in the test solution reacts with the pyridine. It also transmits the fluorescent light back to the detection system. Suitable laser sources include argon laser, carbon dioxide laser, ruby laser, copper vapor laser and the like. Necessary illumination, coupling and detection systems and equipment for use with the subject optode and method are described in U.S. Ser. No. 445,619 which is incorporated herein by reference. The subject optrode is employed for the quantitative detection and monitoring of the levels of halohydrocarbons in groundwater, environmental and tissue samples.

The optrode comprises a tube, preferably a capillary tube, 0.1 mm to 2 mm in internal diameter, preferably capped at one end, although capping is not critical for the operation of the optrode. The capping material is either porous or semipermable, preferably semipermeable. The most preferred capping material is a water impermeable membrane which is also impermeable to the reagents being used, but permeable to halohydrocarbons. Exemplary membrane materials include but are not limited to parafilm (thin paraffin films), mylar, electrostatically treated mylar, zeflour, polycarbonate films and the like. The membrane serves not only to preserve the integrity of the reagents but also provides the required specificity to the analyses as different organochlorides exhibit different rates of permeability.

In an alternative embodiment of the instant optrode, a small cuvette with two compartments may be employed. The cuvette may be of similar dimensions as the capillary tube or slightly larger. The first and second reagents are contained in each of the two compartments. The compartmentalized cuvette is provided with a window between the compartments so as to provide a surface of contact between the first and second reagents. A fiber optic is attached at a first or distal end thereof to the window of the container and adjacent the surface of contact, a second or proximate end of the fiber optic being connected to an illumination source and a detector means.

The method of the present invention comprises the two phase version of the Fujiwara reaction. Although under normal laboratory conditions and conventional methods of detection, both the one phase and two phase approaches work equally well for the detection of gem-halogen organo compounds, with the optrode sensor, the two phase method has certain advantages. The detection of the halohydrocarbons is not affected by the fact that pyridine and, water which is needed for the reaction and as a solvent for the potassium or sodium hydroxide, are immiscible. The construction of the optrode provides for the continual replenishment of the reactants. The general reaction scheme of the subject method is shown in equation 2 below:

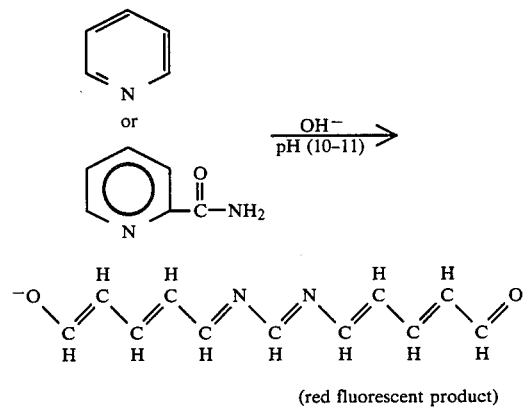

(red fluorescent product)

The pyridine derivative and alkali are layered and contained in a suitable container means such that there is a surface of contact between the two reagents. As used herein, the term pyridine derivative includes pyridine, whether specified separately or not. When exposed to a solution of the analyte which is a halohydrocarbon, or to a solution suspected of containing the analyte, the pyridine derivative reacts with the halohydrocarbon in the test solution in the presence of the alkali to yield a detectable, red fluorescent product. As used herein, the term pyridine derivative includes without limitation, pyridine, salts thereof, substituted pyridine, and related compounds. The amount or the rate of production of the detectable product is measured by the optrode which is positioned adjacent to the surface of contact, and in conjunction with a detection system such as a fluorimeter or spectrometer. The amount of the product formed may be measured continually or at predetermined time intervals.

According to one preferred embodiment of the subject method, the alkali is sodium hydroxide, potassium hydroxide, lithium hydroxide and the like, sodium and potassium hydroxide being preferable. The second reagent is a pyridine or pyridine derivative, exemplary compounds including but not limited to pyridine or pyridinium salts, pyridine carboxaldehyde, pyrazine, pyridine dicarboxylic acids, dimethyl pyridine, methyl pyridine, nicotinamide, isonicotinamide, nicotine-diamide, and the like. Pyridine and nicotinamide are the preferred reagents. Organic halohydrocarbons detectible by the subject method using the instant optrode include but are not limited to gem-halohydrocarbons such as chloroform, methylchloroform, sym-tetrachloroform, phenylchloroform, carbon tetrachloride, dichloromethane, trichloroethylene, 1,1,2-trichloroethane and the like. When the pyridine or pyridine-like compound comes into contact with the halohydrocarbon in an alkaline medium, a bright colored or fluorescent product results. This product is excited at the appropriate wavelength with incident light from a suitable source, and the fluorescence intensity is detected by the optrode at the interface of the pyridine and alkaline phases and is measured as a function of time by means of a suitable detector system such as a spectrometer or a fluorometer. The optrode serves the dual function of trasmitting light from the source to the interface where the fluorescent product is formed and of transmitting the fluorescenct light signal from the product at the interface to the detector system.

Providing a two phase system and a discrete interface between the pyridine phase and the alkaline phase serves to eliminate the problem of pyridine dilution by water permeation and a continual generation of the fluorescent product at the interface is facilitated.

In accordance with another embodiment of the subject method, laser based remote fiber spectrometry is employed for the detection and measurement of trace to macro concentrations of halogenated hydrocarbons from single or multiple samples, from the same location or multiple locations, at a site remote from the detection system. A network of single strand fiber optics or fiber optic cables tipped by appropriate optrodes are placed at various field locations. A laser light of the appropriate wavelength is focused into these single strand optical fibers or cables. The optical fibers or cables are coupled to various samples of the analyte at various locations or from the same locus through the optrodes. The light, after interaction with the analyte, is collected and transmitted back through the same optical fibers or cables to a specially designed detection system such as a spectrometer where the returning light is spectrally sorted and analyzed.

The following examples best serve to illustrate the principle of the subject invention and describe preferred embodiments thereof and are not to be construed as limiting the invention in any manner or to any precise form:

EXAMPLE 1

The Construction Of The Optrode

The optical fiber was purchased from Valtec, Boylston, Massachusetts. It had a 245 μm glass core, a silicon clad, and a polyvinyl sheath. It had an outer diameter of 500 μm. The end of the fiber was carefully polished using a 30 through 1 micron lapping film according to methods known in the art. Approximately 1.2 cm of the clad and buffer were then removed from the polished end. The stripped fiber was immersed in concentrated sulfuric acid to assure that all the cladding had been removed. The acid-cleaned fiber was then washed in distilled water and dried. A 25 μl capillary tube was selected which loosely fitted over the sheather portion of the fiber optic. The fiber was placed in this capillary tube so that the tip of the stripped end was about 1.5 cm from the edge. The capillary was then filled with EPO-TEK 301 epoxy (Epoxy Technology, Inc., Billerica, Mass.) from the back end where the sheathed fiber was located, by pulling a vacuum at the other end of the capillary where the stripped fiber was located, until about 2 mm of the bare fiber was covered. 10.75M KOH was then injected into the open end of the capillary using a very fine needle and a micro syringe until it was just below the end (about 1 mm). Spectral grade pyridine was then injected until its volume equaled that of the KOH. A membrane was glued to the end of the capillary using Light-weld No. 415, UV light curing adhesive, obtained from American Chemical and Engineering, Torrington, Conn. The membrane was made of mylar (polyethylene terephthalates, Dupont, Wilmington, Del. whose surface had been electrostatically etched. Once the adhesive was cured and the membrane was tightly bonded to the end of the capillary, the same glue was applied behind the membrane on the outside of the capillary and a retaining sleeve was pulled over the membrane onto the capillary and UV cured. The sleeve was stretched so that it could be pulled over the capillary. The completed optrode was then placed in a protective shield.

FIG. 1 is a cross-sectional view of the subject optrode 40 shown immersed in test solution 24. The first end of capillary tube 12 is attached to fiber optic 14 by some attaching means such as UV setting epoxy cement 18. A protective sheath 10 is provided for fiber optic 14. A proximate or first end of fiber optic 14 is operationally connected to an illumination source and a detector means, such as a fluorimeter or spectromater. Column 16 of an alkaline reagent is disposed adjacent to the first end of capillary tube 12. Column 20 of pyridine or pyridine derivative is disposed next to and in contact with column 16 of the alkaline reagent preferably such that the surface of contact 32 is adjacent the distal end face 30 of fiber optic 14. This configuration ensures that light from fiber optic 14 illuminates pyridine column 20 where the concentration of OH$^-$ and consequently of the Fujiwara product is highest. The second end 34 of capillary tube 12 is preferably capped by a semipermeable membrane 26 glued or fixed to the capillary tube by some attaching means such as epoxy cement 28 or by welding. Membrane 26 is preferentially permeable to halogenated hydrocarbons but impermeable to pyridine and water. For volatile halohydrocarbons, membrane 26 may be replaced by a bubble.

Figure 2:
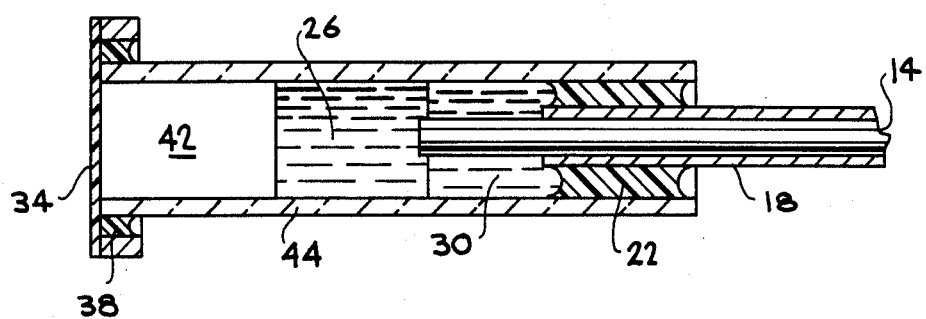
FIG. 2 shows the detailed construction of the optrode, according to one preferred embodiment of the subject invention.

FIG. 2 is a detailed diagram showing the various components thereof. The six key components are (1) the glass-core fiber optic 14, with its optional cladding 18, (2) the glass capillary 44 which houses the optrode components attached with a suitable seal 22 and reagents, (3) pyridine or pyridine-based reagent 26 which is the indicator compound for the halohydrocarbons, (4) alkali reagent 30 to maintain the pH of pyridine at about 10, (5) a membrane such as a paraffin or mylar film 34 to keep the pyridine 26 inside the optrode and the water outside the optrode, while passing the halohydrocarbons, and (6) a shield 38 to protect the optrode while in use; and an optional air space 42 included to help further to keep water out of the optrode.

EXAMPLE 2

Nicotinamide As The Indicator Compound

Figure 4:
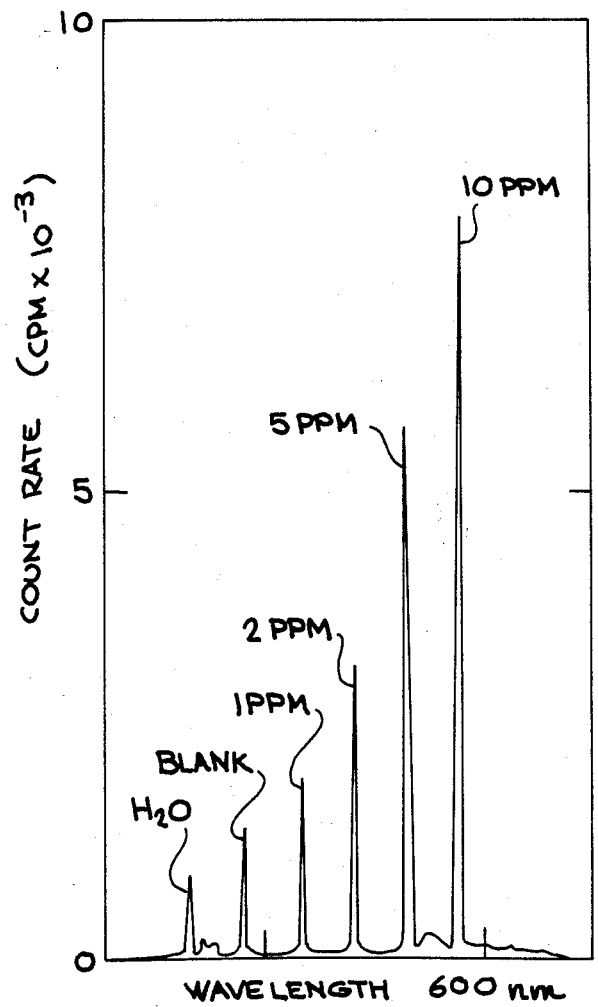
FIG. 4 shows spectra of nicotinamide fluorescence with 5 ppm of $CHCl_3$ present.
Figure 3A:
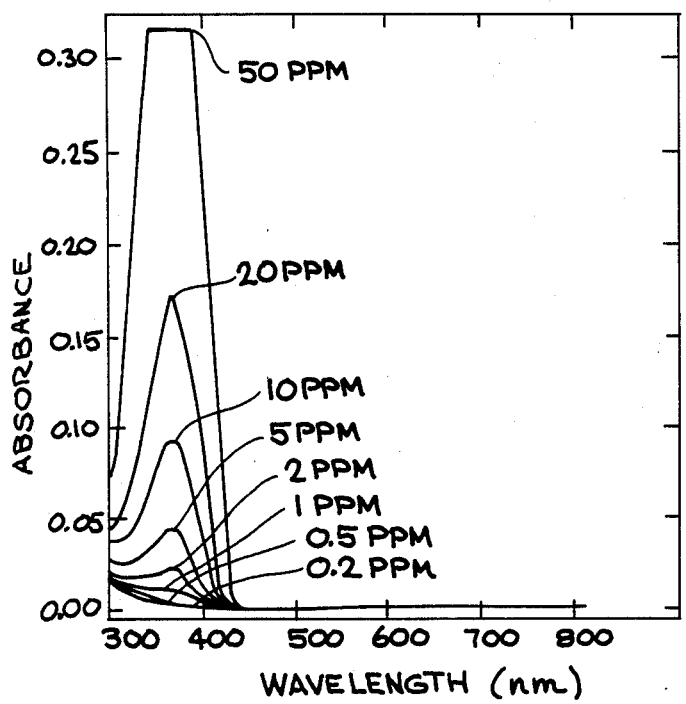
FIG. 3 shows absorption spectra obtained for samples of nicotinamide to which varying amounts of chloroform were added.
Figure 3B:
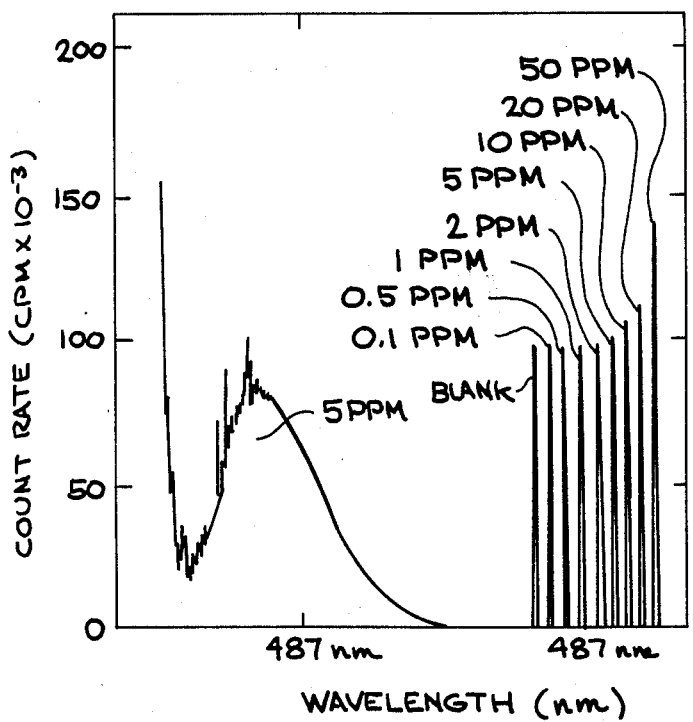

These experiments for the detection of $RCl_{(2+n)}$ were based on the reaction of chloroform ($CHCl_3$) with nicotinamide. FIG. 3 shows absorption spectra obtained for samples of nicotinamide to which varying amounts of chloroform were added. A strong absorption peak observed at 372 nm changed with $CHCl_3$ concentration. When these nicotinamide-$CHCl_3$ mixtures were irradiated at this wavelength, a fluorescence emission at 467 nm was observed whose intensity was $CHCl_3$ concentration dependent. Experiments were also run in the visible range with excitation of nicotinamide-$CHCl_3$ samples at 415 nm which fluoresced at 487 nm. FIG. 4 shows spectra of nicotinamide fluorescence with 5 ppm of $CHCl_3$ present. The measurements indicated that the nicotinamide system was essentially pH independent and that it was very insoluble in water which are important in sensor applications.

EXAMPLE 3

Pyridine As The Indicator Compound

Pyridine exhibits a strong absorption peak at 372 nm and a weaker one at 530 nm. The absorption at 372 changed predictably with the addition of $CHCl_3$. The strength of the absorption at 530 nm was chosen for measurement as a function of $CHCl_3$ concentration to determine if absorption levels at the weaker 530 nm peak could be utilized for measuring low levels of chloroform. Alternatively, when employing an argon laser irradiation source, the 488 nm or the 514 nm absorption peaks were used to measure the levels of chloroform. FIG. 5 shows that using the 530 nm absorption peak, $CHCl_3$ concentrations of less than 1 ppm could still be measured. Pyridine and KOH are purchased as analytical reagents. Distilled water is used in the preparation of all reagents. The pyridine is used in the pure state where as KOH is made into a 10.75 M aqueous solution. It is critical to control KOH concentration as it affects the water content of the system. 10.75 M KOH keeps the water concentration at the optimum 7%. If the KOH molarity is too low, the spectral absorbance at 535 nm increases until it reaches the maximum and then decreases as increasing amounts of water diffuse into the pyridine phase. If the amount of KOH is too high, a maximum absorbance is never attained because there is an insufficient amount of water and KOH would be present in the pyridine phase. KOH concentrations between 10 and 11 M worked the best.

The optrode and method of the subject invention are thus are suitable for monitoring volatile organic chloride contaminants in aqueous systems. The subject optrode is able to detect and quantify sub-part-per-million concentrations of organic chlorides in aqueous solutions. The fiber optic system used in the subject invention enables the measurement of organic chloride where the sample and detection system are separated by a distance of greater than 500 meters of optical fiber. It is also possible by the use of the subject method to simultaneously measure organic chloride content in multiple samples from the same location or from different locations that are not too far apart. The subject method is specific to organic compounds containing two or more chlorines and sensitive to 0.1 part per million, and reproducible within ±3%. The method is also free from interferences from other constituents in the sample when the end of the capillary is capped by a semipermeable membrane. The optrode has a useful shelf life as it is stable in aqueous systems for more than three months.

The above embodiments were chosen and described in order to explain best the principles and the practical applications of the subject invention thereby to enable those skilled in the art to utilize the invention in various other embodiments and various modifications as are suitable for tne particular use contemplated. The foregoing description of some preferred embodiments of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

We claim:

1. As an article of manufacture an optrode for chemically sensing halogenated hydrocarbons comprising the elements:

a capillary tube capped at one end by a semipermeable membrane of porous membrane;

a fiber optic attached at a distal end thereof to a second end of said capillary tube by attaching means, said fiber optic extending into said capillary tube, a proximal end of said fiber optic being connected to an illumination source and a detector means;

a column of a first reagent comprising pyridine or a pyridine derivative disposed in said capillary tube adjacent said capped end; and a column of a second reagent comprising an alkali disposed in said capillary tube adjacent to and in contact with said column of said first reagent such that a surface of contact between said alkali and said first reagent is adjacent said distal end of said fiber optic.

2. The optrode of claim 1 wherein said first reagent is pyridine and said alkali is selected from the group consisting of potassium hydroxide, sodium hydroxide and lithium hydroxide.

3. The optrode of claim 2 wherein said alkali reagent iss potassium hydroxide.

4. The optrode of claim 3 wherein said membrane is selected from a group consisting of mylar, paraffin film, electrostatically treated mylar and polycarbonate films.

5. As an article of manufacture, a two-phase detection system comprising:

a capillary tube capped at one end by a semipermeable membrane or porous membrane;

a sensor means attached to a second end of said capillary tube by attaching means so as to extend into said capillary tube, a second end of said sensor means being connected to a detector means;

a column of a first reagent comprising pyridine or a pyridine derivative disposed in said capillary tube adjacent to said capped end thereof;

a column of a second reagent comprising an alkali disposed in said capillarly tube adjacent to and in contact with said column of said first reagent such that a surface of contact between said alkali and said first reagent is adjacent the second end of said sensor means; and said capped end of said capillary tube being adapted to be placed in contact with a solution of an analyte containing a halogenated hydrocarbon.

6. The article of claim 5 wherein said alkali is potassium hydroxide and said first reagent is pyridine.

* * * * *